United States Defensive Publication [19] (H) [11] T102,909

Cruickshank et al. [43] Apr. 5, 1983

[54] INTERMEDIATES AND PROCESS FOR INSECTICIDAL BIPHENYLMETHYL ESTERS

[76] Inventors: Philip A. Cruickshank, 211 Dodds La., Princeton, N.J. 08540; Anthony J. Martinez, 20 Weyburne Rd., Hamilton Square, N.J. 08690

[21] Appl. No.: 415,004

[22] Filed: Sep. 7, 1982

Related U.S. Application Data

[63] Continuation of Ser. No. 286,489, Jul. 24, 1981, abandoned.

[51] Int. Cl.[3] ..... C07C 69/533

[52] U.S. Cl. ..... 560/221; 560/227; 560/124

[57] ABSTRACT

Compounds of formulae II, III and IV:

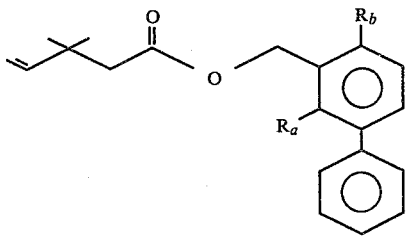

II

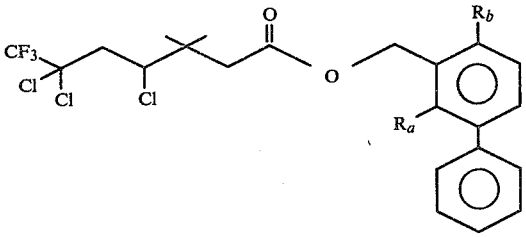

III

-continued

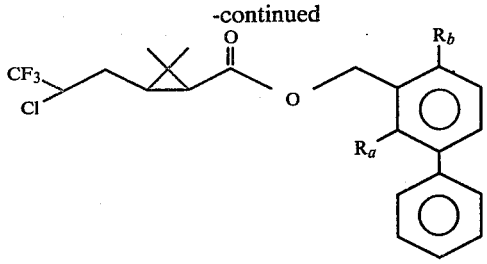

IV are useful intermediates for preparation of an insecticidal compound of formula (I)

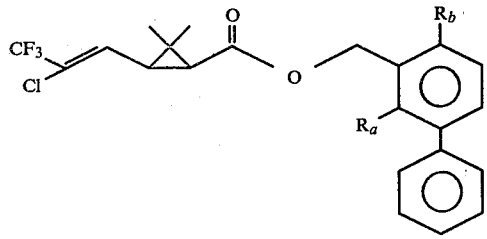

I in which $R_a$ and $R_b$ are independently hydrogen, halogen, or alkyl. The intermediate II is prepared by reacting 3,3-dimethyl-4-pentenoic acid, a salt thereof, a lower alkyl ester or an acid chloride thereof with a compound of the formula

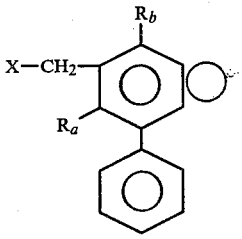

in which X is hydroxy or a good leaving group.

Intermediate III is prepared by reacting II with 1,1,1-trichloro-2,2,2-trifluoroethane in the presence of a solvent and catalyst. Intermediate III is then dehydrohalogenated in the presence of base to remove 2 moles of halogen halide per mole of III in one or two steps to produce I.

1 Claim, No Sheets Drawing,

20 Pages Specification

The file of this unexamined application may be inspected and copies thereof may be purchased (849 O.G. 1221, Apr. 9, 1968).